United States Patent [19]

Muisers et al.

[11] 4,417,037
[45] Nov. 22, 1983

[54] VINYL ACYLANHYDROCITRATES AND THEIR PREPARATION

[75] Inventors: Hans-Ferdinand Muisers; Dieter Arlt, both of Cologne; Manfred Jautelat, Burscheid; Heinrich Alberts, Odenthal; Fritz Mietzsch, Bergisch-Gladbach, all of Fed. Rep. of Germany

[73] Assignee: Bayer Aktiengesellschaft, Leverkusen, Fed. Rep. of Germany

[21] Appl. No.: 458,793

[22] Filed: Jan. 18, 1983

[30] Foreign Application Priority Data

Feb. 6, 1982 [DE] Fed. Rep. of Germany ....... 3204127

[51] Int. Cl.³ ..................... C08F 18/14; C08F 118/14; C07D 307/32
[52] U.S. Cl. .................... 526/271; 549/253; 526/272
[58] Field of Search ................. 526/271, 272; 549/253

[56] References Cited

U.S. PATENT DOCUMENTS 3,441,543  4/1969  Heilman ........................... 526/271
4,282,156  8/1981  Gutierrez ......................... 549/253

FOREIGN PATENT DOCUMENTS 46-3987  1/1971  Japan ................................. 526/271

Primary Examiner—Joseph L. Schofer
Assistant Examiner—Peter F. Kulkosky
Attorney, Agent, or Firm—Sprung, Horn, Kramer & Woods

[57] ABSTRACT

A vinyl acylanhydrocitrate of the formula

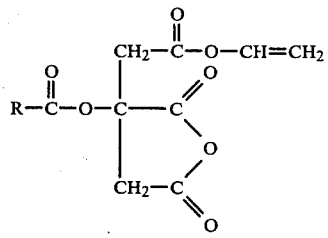

in which
R denotes hydrogen or lower alkyl is disclosed. The vinyl acylanhydrocitrates can be prepared by initially contacting citric acid with a carboxylic anhydride or carbonyl chloride followed by transesterification of the reaction product either with vinyl acetate in the presence of a catalyst or with acetylene. The vinyl acylanhydrocitrates can be polymerized or copolymerized to form useful products useful for inclusion in adhesive compositions, for crosslinking in coating systems and duromers or, after ring opening with bases, as dispersing auxiliaries or agents to increase the viscosity of aqueous systems.

16 Claims, No Drawings

VINYL ACYLANHYDROCITRATES AND THEIR PREPARATION

The present invention relates to new vinyl acylanhydrocitrates and a process for their preparation.

Final products, especially in polymer chemistry, as a rule are based on starting materials which are derived from petroleum. With the general shortage of petroleum products there is, in the development of new products, a need to proceed from starting materials which are independent of petroleum and which are continuously being produced.

The present invention relates to new vinyl acylanhydrocitrates which are derived from citric acid. Citric acid is produced in large amounts by fermentation of carbohydrates (for example maize starch or molasses), and is conveniently available due to its production from natural waste products.

The new vinyl acylanhydrocitrates correspond to the formula (I)

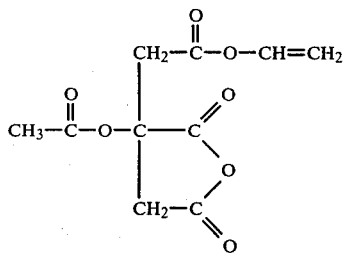

in which

R denotes hydrogen or lower alkyl.

According to the invention, lower alkyl denotes a straight-chain or branched hydrocarbon radical having 1 to, say, 6 carbon atoms. Examples which may be mentioned are: methyl, ethyl, propyl, isopropyl, butyl, isobutyl, pentyl, isopentyl, hexyl and isohexyl.

The preferred vinyl acylanhydrocitrate is the compound of the formula (II)

$$\text{(II)}$$

(structure shown)

Vinyl acylanhydrocitrates can be prepared by initially reacting citric acid with a carboxylic anhydride or a carbonyl chloride and then transesterifying with vinyl acetate in the presence of a catalyst or by introducing acetylene.

The process according to the invention is preferably carried out as a "one-pot process".

The process according to the invention can, for example, be illustrated by the following equation:

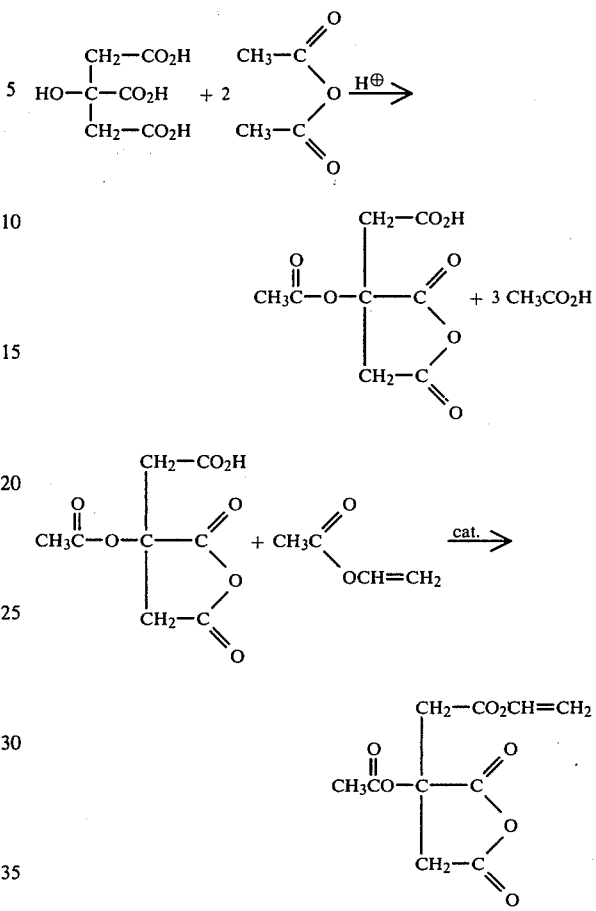

Carboxyclic anhydrides according to the invention are anhydrides of lower organic carbon acids. They can be described by the formula

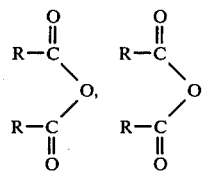

in which R has the meaning given above.

Carbonyl chlorides according to the invention are carbon acid chlorides of lower organic acids. They can be described by the formula

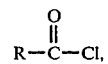

in which R has the meaning given above.

Preferred for the process of invention is acetic anhydride.

The process according to the invention is generally carried out in the temperature range of 40° to 110° C., preferably of 50° to 70° C. In general, the reaction is carried out under normal pressure (about 1 bar) or under elevated pressure (up to about 3 bar). The process according to the invention is preferably carried out under normal pressure.

The first reaction step is carried out according to the invention in such a manner that anhydrous citric acid is reacted with the stoichiometric amount or an excess (up to 3 mol/mol of citric acid) of carboxylic anhydride or carbonyl chloride, preferably the stoichiometric amount of carboxylic anhydride, in the temperature range according to the invention. It is advantageous to add small amounts of an acid catalyst. Examples of acid catalysts are concentrated sulphuric acid, phosphoric acid or boron trifluoride etherate. The amount of the catalyst according to the invention is generally 0.01 to 0.1% by weight relative to the citric acid. Preferably, 0.01 to 0.05% by weight of the catalyst, relative to the citric acid, is employed. After completion of the reaction, the acetic acid produced is distilled off under normal pressure (about 1 bar) or decreased pressure (down to about 1 mbar), preferably under decreased pressure.

The residue from the first reaction step is reacted in the second reaction step according to the invention with vinyl acetate in the presence of a catalyst. Suitable catalysts which may be mentioned are palladium salts or mercury salts, preferably mercury salts. The salts generally employed are the halides (fluorides, chlorides, bromides and iodides, preferably the chlorides) and the acetates. Examples which may be mentioned are: palladium(II) and mercury(II) chloride, palladium(II) and mercury(II) acetate. Mercury(II) acetate is preferably employed.

The amount of the catalyst in the second reaction step is 0.1 to 10% by weight relative to the amount of citric acid employed. An amount of 0.1 to 1% by weight is preferably employed.

The process according to the invention is advantageously carried out with an excess of vinyl acetate. In general, 2 to 10 mol of vinyl acetate, preferably 3 to 5 mol of vinyl acetate, per mol of citric acid employed are used.

After completion of the second reaction step, the catalyst is precipitated as a sparingly soluble sulphide and can thus be removed almost quantitatively. The precipitation is carried out by the addition of an equimolar amount of a suitable sulphur compound. Suitable sulphur compounds are those which dissolve in vinyl acetate and acetic acid to a significant extent and form a sulphide with the catalyst.

Examples of suitable precipitants for the catalyst are hydrogen, sulphide, metal sulphides, for example sodium sulphide, organic thio compounds, for example thiocarboxamides, thiourea and alkylated thioureas. Thioacetamide is particularly preferably employed.

The formation of a filterable precipitate of mercury sulphide generally occurs slowly. Thus it is advisable to carry out the addition of the precipitant at the reaction temperature according to the invention and to continue stirring at this temperature for a further 1 to 5 hours, preferably 2 to 3 hours.

The removal of the precipitate of mercury sulphide is carried out in such a manner that the warm reaction solution is filtered with suction through a suitable filtration auxiliary. Suitable filtration auxiliaries are active charcoal, silica gel, kieselguhr and fuller's earth, preferably fuller's earth.

On cooling the filtrate down, the desired product precipitates out to a large extent and can be removed in a manner known per se, for example by filtration with suction.

In a modified embodiment of the process according to the invention, after completion of the first reaction step, the catalyst can be added to the reaction solution and acetylene introduced under pressure (preferably up to 3 bar) or at normal pressure, preferably at normal pressure. In this case, the amount of catalyst is preferably 0.1 to 10% by weight, particularly preferably 0.2 to 2% by weight, relative to the amount of citric acid employed.

For the introduction of acetylene in the second reaction step, this is preferably carried out in the temperature range from 0° to 100° C., particularly preferably at room temperature (at about 20° C.).

Vinyl acylanhydrocitrates can be copolymerised with various monomers. Examples of monomers which may be mentioned are: vinyl compounds, such as styrene, vinyl chloride or carboxylic esters of vinyl alcohol, derivatives of (meth)acrylic acid, in particular their esters, ethylene and alpha-olefines.

New polymers, which contain a reactive carboxylic anhydride group, are obtained by copolymerisation of the vinyl acylanhydrocitrates according to the invention with monomers which are known per se.

Polymers, which contain a carboxylic anhydride group, have been hitherto prepared by copolymerisation with maleic anhydride (literature: Houben-Weyl "Methoden der Organischen Chemie" (Methods of Organic Chemistry) Volume XIV/1, Georg Thieme-Verlag, Stuttgart). In the copolymerisation, maleic anhydride is incorporated in the polymer alternately and in the molar ratio of 1:1. This is disadvantageous for most industrial purposes. Lower extents of incorporation and a statistical distribution of anhydride groups are desired, since otherwise the polymer becomes brittle and is sensitive to water and alkalis.

In the copolymerisation of the vinyl acylanhydrocitrates according to the invention, this component is not incorporated alternately. Thus it is possible, in a surprising manner, to fix the amount of the vinyl acylanhydrocitrate component within wide limits.

The new polymers can, due to their reactivity, be employed for many purposes; thus, for example, they can be employed to improve the adhesion in adhesives, for cross-linking in coating systems and duromers or, after ring-opening with bases, as dispersing auxiliaries or to increase the viscosity in aqueous systems.

EXAMPLE 1

3,630 g (15 mols) of anhydrous citric acid, 3,060 g (30 mols) of acetic anhydride and 0.5 ml of concentrated sulphuric acid are stirred at about 60° C. for about 6 hours. The acetic acid produced is almost completely distilled off under water-pump vacuum. 3,870 g (45 mols) of vinyl acetate and 24 g of mercury(II) acetate are added to the solidified residue and the mixture is stirred at about 60° C. After 12 hours, 5.7 g of thioacetamide are added, the mixture is stirred at the same temperature for approximately a further 2 hours and is then filtered off with suction over Tonsil. The mercury content of the filtrate is about 1 ppm.

After some time, 1,630 g (45%) of the desired product precipitate from the filtrate. It can be recrystallised in toluene (melting point: 108° C.).

EXAMPLE 2

1 mol of anhydrous citric acid and 2 mols of acetic anhydride are stirred, after the addition of one drop of concentrated sulphuric acid, at 60° C. for about 6 hours. The acetic acid produced is almost completely distilled off under water-pump vacuum. 4 mols of vinyl acetate and 3.5 g of palladium(II) chloride are added to the solidified residue and the mixture is boiled under reflux for 8 hours. After completion of reaction, 15 g of active charcoal are added and the reaction mixture is filtered hot. The filtrate is concentrated. According to the nuclear magnetic resonance spectrum, the solidified residue contains about 10% of vinyl acetylanhydrocitrate.

EXAMPLE 3

1 mol of anhydrous citric acid and 2 mols of acetic anhydride are stirred, after the addition of one drop of concentrated sulphuric acid, at 60° C. for 6 hours. Then 2 g of mercury(II) acetate and 2 g of boron trifluoride etherate are added and acetylene is introduced at room temperature. The reaction temperature should not exceed 30° C. The reaction solution assumes a dark brown to black colouration. After about 2 mols of acetylene have been introduced, the precipitate is filtered off with suction and is washed with a little cold vinyl acetate.

72 g of vinyl acetylanhydrocitrate are isolated.

EXAMPLE 4

88 g of vinyl acetylanhydrocitrate, 207 g of ethyl acetate and 350 mg of azobisisobutyronitrile are placed in a 1 l high-pressure autoclave. After displacing the air with ethylene, the mixture is heated at 70° C. for 12 hours and the ethylene pressure is maintained constant at 300 bar during this. A polymer suspension is obtained which, after filtration and drying, provides 57 g of polymer. The molar ratio of vinyl acetylanhydrocitrate to ethylene in the polymer is 0.29:1 according to elementary analysis.

EXAMPLE 5

The procedure is as in Example 4 but with 14.5 g of vinyl acetylanhydrocitrate and 300 g of tert.-butanol instead of ethyl acetate. In this case, 40 g of a polymer are obtained, which contains the vinyl acetylanhydrocitrate component in a molar ratio of 0.08:1.

EXAMPLE 6

Examples 4 and 5 are repeated but with maleic anhydride instead of vinyl acetylanhydrocitrate. The yields are 97 and 16 g of polymer respectively; the molar ratio of maleic anhydride to ethylene is 0.96:1 in both cases.

What is claimed is:

1. A vinyl acylanhydrocitrate of the formula

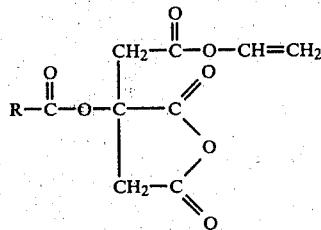

in which
R denotes hydrogen or lower alkyl.

2. Vinyl acylanhydrocitrate according to claim 1 of the formula

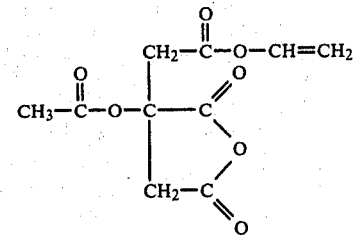

3. A process for the preparation of a vinyl acylanhydrocitrate which comprises initially contacting citric acid with a carboxylic anhydride or a carbonyl chloride and thereafter transesterifying the resultant product with:
   A. Vinyl acetate in the presence of a catalyst; or
   B. Acetylene.

4. A process according to claim 3 wherein the reaction product is transesterified by contacting the same with vinyl acetate in the presence of a mercury(II) or palladium(II) salt as catalyst.

5. A process according to claim 3 wherein the process of invention is carried out at a temperature in the range from 40° to 110° C.

6. A process according to claim 3 wherein the reaction product obtained by contacting the citric acid with carboxylic anhydride or carbonyl chloride is transesterified with acetylene.

7. A process according to claim 4 wherein a mercury(II) salt is employed and, after completion of the reaction, the mercury catalyst is precipitated as mercury sulphide by adding a sulphur compound to the reaction mixture.

8. A process according to claim 7 wherein said sulphur compound is thioacetamide.

9. A process according to claim 3 wherein the reaction product obtained by contacting citric acid with carboxylic acid anhydride or carbonyl chloride is transesterified with acetylene by introducing acetylene into a solution of acetyl anhydrocitric acid in acetic acid obtained by contacting citric acid with acetic anhydride or acetyl chloride, in the presence of boron trifluoride etherate or boron trifluoride-acetic acid adduct and a mercury(II) salt.

10. A polymer of a vinyl acylanhydrocitrate of the formula

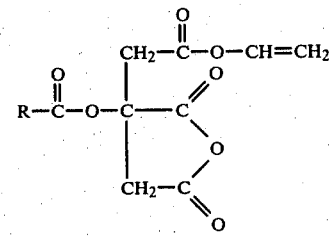

in which
R denotes hydrogen or lower alkyl.

11. A polymer according to claim 10 which is a polymer of a vinyl acylanhydrocitrate of the formula

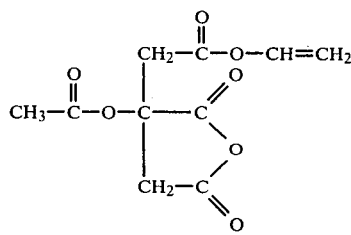

12. A polymer according to claim 10 which is a copolymer of said vinyl acylanhydrocitrate.

13. A copolymer according to claim 12 wherein the comonomer is a vinyl compound.

14. A copolymer according to claim 13 which is the copolymerization product of the said vinyl acylanhydrocitrate and a vinyl compound selected from the group consisting of styrene, vinyl chloride, a carboxylic ester of vinyl alcohol, (meth)acrylic acid or a derivative thereof or mixtures thereof.

15. A polymer according to claim 10 which is a copolymer of said vinyl acylanhydrocitrate and an alpha olefin.

16. A copolymer according to claim 15 wherein said alpha olefin is ethylene.

* * * * *